United States Patent
Wu et al.

(10) Patent No.: US 10,631,998 B2
(45) Date of Patent: Apr. 28, 2020

(54) LUMBAR INTERBODY FUSION CAGE FOR TREATING LUMBAR SPONDYLOLISTHESIS VIA LATERAL APPROACH

(71) Applicants: Aimin Wu, Zhejiang (CN); Xiangyang Wang, Zhejiang (CN); Yixing Huang, Zhejiang (CN); Wenfei Ni, Zhejiang (CN); Yan Lin, Zhejiang (CN); Zhongke Lin, Zhejiang (CN); Hui Xu, Zhejiang (CN)

(72) Inventors: Aimin Wu, Zhejiang (CN); Xiangyang Wang, Zhejiang (CN); Yixing Huang, Zhejiang (CN); Wenfei Ni, Zhejiang (CN); Yan Lin, Zhejiang (CN); Zhongke Lin, Zhejiang (CN); Hui Xu, Zhejiang (CN)

(73) Assignees: The Second Affiliated Hospital of Wenzhou Medical University, Wenzhou, Zhejiang (CN); Yuying Children's Hospital of Wenzhou Medical University, Wenzhou, Zhejiang (CN)

(*) Notice: Subject to any disclaimer, the term of this patent is extended or adjusted under 35 U.S.C. 154(b) by 113 days.

(21) Appl. No.: 15/937,868

(22) Filed: Mar. 28, 2018

(65) Prior Publication Data
US 2018/0360614 A1    Dec. 20, 2018

(30) Foreign Application Priority Data
Jun. 14, 2017 (CN) .......................... 2017 1 0446652

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/8042* (2013.01); *A61F 2/4611* (2013.01);
(Continued)

(58) Field of Classification Search
CPC .... A61F 2/44; A61F 2/447; A61F 2/46; A61F 2/4611
See application file for complete search history.

(56) References Cited

U.S. PATENT DOCUMENTS 8,308,804 B2* 11/2012 Krueger ................. A61F 2/442
                                                     623/17.11
8,591,553 B2* 11/2013 Eisermann ......... A61B 17/1642
                                                     606/279
(Continued)

*Primary Examiner* — Christopher J Beccia

(57) ABSTRACT

The disclosure claims a lumbar interbody fusion cage for treating lumbar spondylolisthesis via a lateral approach. The lumbar interbody fusion cage comprises a supporting frame body, wherein upper and lower blades are mounted on the upper and lower end surfaces of the supporting frame body, a distracting component for driving the upper and lower blades to axially distract along a lumbar interbody and an orthotopic moving component for driving the upper and lower blades to move along the lumbar interbody back and forth are mounted in the supporting frame body, the upper and lower blades respectively extend to form lateral lobes, fixing holes through which fixing nails penetrate are formed on the lateral lobes, the fixing nail of the upper lateral lobe penetrates backward from bottom to top in a slanting way to give a certain rear thrust to the slipped lumbar vertebrae and help reduction of the lumbar spondylolisthesis, and the fixing nailing of the lower lateral lobe penetrates forward from top to bottom to give a forward thrust to the lumbar vertebrae and help the reduction of the lumbar spondylolisthesis. The lumbar interbody fusion cage can solve both an intervertebral spacing and dislocation arisen from forward
(Continued)

and backward lumbar spondylolisthesis, has easy operation and small pain to patients, and is safer and more reliable.

10 Claims, 9 Drawing Sheets

(51) Int. Cl.
 *A61B 17/80* (2006.01)
 *A61F 2/30* (2006.01)
 *A61F 2/28* (2006.01)

(52) U.S. Cl.
 CPC ... *A61F 2/30771* (2013.01); *A61F 2002/2835* (2013.01); *A61F 2002/30383* (2013.01); *A61F 2002/30507* (2013.01); *A61F 2002/30537* (2013.01); *A61F 2002/30553* (2013.01); *A61F 2002/30556* (2013.01); *A61F 2002/30578* (2013.01); *A61F 2002/30843* (2013.01)

(56) References Cited

U.S. PATENT DOCUMENTS

| | | | | |
|---|---|---|---|---|
| 8,906,099 | B2* | 12/2014 | Poulos | A61F 2/4611 |
| | | | | 623/17.16 |
| 9,220,547 | B2* | 12/2015 | Blain | A61B 17/7059 |
| 9,233,009 | B2* | 1/2016 | Gray | A61F 2/442 |
| 9,526,628 | B2* | 12/2016 | Krueger | A61F 2/442 |
| 9,592,131 | B2* | 3/2017 | Sandstrom | A61F 2/4455 |
| 9,707,100 | B2* | 7/2017 | Duffield | A61F 2/4611 |
| 9,987,142 | B2* | 6/2018 | McConnell | A61F 2/4455 |
| 10,085,855 | B2* | 10/2018 | Ty | A61F 2/4465 |
| 10,307,265 | B2* | 6/2019 | Sack | A61F 2/447 |

* cited by examiner

LUMBAR INTERBODY FUSION CAGE FOR TREATING LUMBAR SPONDYLOLISTHESIS VIA LATERAL APPROACH

BACKGROUND OF THE INVENTION

1. Field of the Invention

The disclosure belongs to the technical field of a lumbar interbody fusion cage for treating lumbar spondylolisthesis, and particularly claims a lumbar interbody fusion cage for treating lumbar spondylolisthesis via a lateral approach, which can play a role of distraction and reduction of spondylolisthesis for the lumbar spondylolisthesis.

2. Description of the Related Art

A lumbar interbody fusion cage is applied to a lumbar interbody fusion, and plays an important role for treatment of a discogenic low back pain. Currently, the lumbar interbody fusion can be implanted in an intervertebral space between upper and lower sections of vertebrae, and can be disclosed through a distractable lumbar interbody fusion cage, such as a document with a Chinese patent number of ZL201620502029.4, and a distracting body thereof comprises a fixing block and an adjustable distracting block, wherein the tail of the adjustable distracting block is hinged with the tail of the fixing block, a distracting mechanism adjusts the adjustable distracting block to distract the intervertebral space, and bone grafting is performed in the intervertebral space of the vertebra, thereby effectively recovering an intervertebral space height and volume of an intervertebral foramen. But for patients with anterior and posterior shifting of the upper and lower sections of vertebrae, a posterior lumbar interbody fusion is usually adopted when treatment, the lumbar interbody fusion cage enters the intervertebral space via the posterior approach, is fixed by upper and lower bone nails, and thus, plays a role of reduction for vertebra with anterior and posterior shifting. But the posterior lumbar interbody fusion has damages to human glass muscles, such as big soft tissue injury, big trauma and much bleeding.

For example, for the existing fusion cage mentioned in the document "Lumbar Interbody Fusion Cage for Spinal Implantation" with Chinese Patent number of ZL201510451399.X, the anterior approach only could be used for the front, and the lateral approach only could be used for the side, but in an actual operation, the anterior approach could not be replaced with the lateral approach, and similarly, the lateral approach or the anterior approach could not be replaced with the posterior approach. To reduce expenses of medical consumables, the document designs a lumbar interbody fusion cage for inserting from a front, a side and an inclined surface of a spine, which could be inserted from the side, but could not have a reduction function of adjusting the anterior and posterior shifting of the upper and lower sections of vertebrae. In case of achieving this function, it still should cooperate with the lumbar interbody fusion cage via the posterior approach.

SUMMARY OF THE INVENTION

To overcome the deficiency of the existing technology, the disclosure provides a lumbar interbody fusion cage for treating lumbar spondylolisthesis via a lateral approach. The lumbar interbody fusion cage has effects of external supporting and the reduction of forward and backward spondylolisthesis for upper and lower sections of vertebrae.

To achieve the above purpose, the technical solution adopted by the disclosure is that: a lumbar interbody fusion cage for treating lumbar spondylolisthesis via a lateral approach, comprising a body frame, supporting lobes and a fixing nail, wherein the body frame comprises an implantation end and a tail end, a frame body structure having a hollow cavity is formed between the implantation end and the tail end through a connection of a front side wall and a rear side wall, a bone grafting hole connected to the hollow cavity is formed at the tail end, the supporting lobes are distributed on the upper and lower end surfaces of the body frame, and each of the supporting lobes is provided with a center hole connected to the hollow cavity; an external supporting structure for driving the supporting lobes to externally expand towards the upper and lower end surfaces and a reduction moving structure for driving the two supporting lobes to move towards the front side wall and the rear side wall respectively are in sliding fit with the body frame; the hollow cavity comprises two ports located on the upper and lower end surfaces of the body frame, and a mounting cavity fitted with the supporting lobe, an external supporting track fitted with the external supporting structure and a reduction moving track fitted with the reduction moving structure are distributed between the two ports of the upper and lower end surfaces; and the supporting lobes are in close fit with the left and right inner walls of the mounting cavity and in clearance fit with the upper and lower inner walls of the mounting cavity, a lateral lobe is arranged at a side that the supporting lobe is close to the tail end of the body frame and is equipped with a fixing hole, a fixing nail slanted above a rear side is fitted in the fixing hole of the lateral lobe located on the upper end surface, and a fixing nail slanted below a front side is fitted in the fixing hole of the lateral lobe located on the lower end surface. After the lumbar interbody fusion cage enters an intervertebral space from sides of upper and lower sections of vertebrae, the supporting lobes are enabled to externally expand towards the upper and lower end surfaces for distracting through the external supporting structure, the upper and lower supporting lobes may be driven through the reduction moving structure to respectively move towards the front side wall and the rear side wall along a horizontal direction, thereby giving a reduction effect to spondylolisthesis of the upper and lower sections of vertebrae.

Further, the external supporting structure comprises an external supporting frame; the external supporting frame is equipped with a guide bar which is in sliding fit with the external supporting track, two groups of abutted bevels are respectively arranged on the upper and lower end surfaces of the external supporting frame and respectively located at the left side end and the right side end of the external supporting frame, the two groups of abutted bevels on the upper and lower end surfaces extend towards the left side end in a slanting way, a corresponding fitted bevel is arranged on the internal end surface of the supporting lobe, an operation section is arranged on the external supporting frame and is in thread spinning fit with the tail end of the body frame, and the abutted bevel of the external supporting frame is abutted against the fitted bevel with a positive movement of a thread of the operation section to drive the supporting lobe to externally support and move to form an external expansion structure of the supporting lobe; the reduction moving structure comprises a reduction support, the reduction support is equipped with a guide bar which is fitted with the reduction moving track, two groups of wedge-shaped blocks are arranged on the reduction support, two groups of wedge-shaped surfaces are formed on the two groups of wedge-shaped blocks and respectively extend towards the rear side wall and the front side wall from the left side end to the right side end, beveled bumps fitted with the wedge-shaped surfaces are arranged on the internal end surface of the supporting lobe, a bevel of the beveled bump forms a bump fitting surface, and the bump fitting surface is abutted against the wedge-shaped surface; and an operation section which is in thread spinning with the tail end of the body frame is arranged on the reduction support, and the two supporting lobes on the upper and lower end surfaces are abutted against the beveled bumps through the wedge-shaped surface with a positive thread movement of the operation section to drive the two supporting lobes to respectively move towards the front side wall and the rear side wall to form a reduction structure of the supporting lobe. The external supporting structure achieves the external expansion of the supporting lobes through the abutted bevels on the upper and lower end surfaces, the abutted bevels on the upper and lower end surfaces are formed by inclining from the left side end to the right side end towards the upper end surface or the lower end surface, and when the operation section of the external supporting frame convolutes, the externally expanded supporting lobes achieve the reduction through an extrusion effect between the upper and lower sections of vertebrae; and the front and rear sides of the wedge-shaped surface on the reduction support are inclined and extend in the same direction, and when an external force drives the reduction support to move towards the left side end, the supporting lobes on the upper and lower end surfaces move towards the front side end and the rear side end to play a role of adjustment and reduction for the upper and lower sections of vertebrae.

Further, the reduction support and the external supporting frame are in a hollow frame body structure, and are stacked up and down; the reduction moving track and the external supporting track are distributed up and down and are respectively adapted to the guide bar of the reduction support and the guide bar of the external supporting frame; abutted blocks are arranged at the left end and the right end of the external supporting frame; the abutted bevels are arranged on the upper end surface or the lower end surface of the abutted blocks; the wedged-shaped blocks are arranged at the left end and the right end of the reduction support; the wedge-shaped surface is arranged at the left side or the right side of the wedge-shaped block; and the abutted blocks are located in a space formed by the wedge-shaped blocks at the left and right ends, and a gap is formed between the abutted blocks and the wedge-shaped blocks and comprises a front end gap, a rear end gap, a left side gap and a right side gap. The reduction support and the external supporting frame are stacked up and down, and the wedge-shaped block on the reduction support is located outside to move towards the front side wall or the rear side wall horizontally; and an abutted inclined block on the external supporting frame is located inside, a gap is formed between the abutted inclined block and the wedge-shaped block, namely, a gap is formed between the front end of the abutted inclined block and the wedge-shaped block, and a gap is formed between the rear end of the abutted inclined block and the wedge-shaped block, thereby facilitating noninterference of forward and backward movement of the external supporting frame and forward and backward movement between the reduction supports.

Further, a mounting hole is formed at the rear side of the external supporting frame; the operation section of the external supporting frame comprises a thread portion and a connecting shaft portion, one end of the connecting shaft portion of the external supporting frame penetrates through the mounting hole of the external supporting frame and then is fixed with a rivet, and the other end thereof is integrally connected with the thread portion; a mounting hole is formed at the rear side of the reduction support; the operation section of the reduction section comprises a thread portion and a connecting shaft portion, one end of the connecting shaft portion of the reduction support penetrates through the mounting hole of the external supporting frame and then is fixed with a rivet, and the other end thereof is integrally connected with the thread portion of the reduction support; and two thread holes which are respectively in thread fit with the operation section of the external supporting frame and the operation section of the reduction support are formed at the tail end of the body frame. The operation section is connected to the body frame through the thread portion and movably mounted on the external supporting frame through the connecting shaft portion and a rivet, and drives the external supporting frame to move back and forth through the thread rotation; and mounting structures of the reduction support and the operation section thereof are the same as above.

Further, the lateral lobe is equipped with a locking structure of the fixing nail, the locking structure comprises a locking nail, the lateral lobe is equipped with a locking hole for accommodating the locking nail, the side wall of the locking hole is locally connected to the fixing hole, and one end of the locking nail penetrates through the locking hole and is connected to the lateral lobe by rotating with a rivet, the side of the locking nail comprises a convex arc section and a concave arc section formed through cutting, the concave arc section is adapted to a lateral arc-shaped surface of a head of the fixing nail located in a neighboring fixing hole and is in clearance fit with the same, and the convex arc section of the locking nail is in close extrusion fit with the lateral arc-shaped surface of the head of the fixing nail. The fixing nail located at the upper end is arranged by inclining upward and outward, the fixing nail located at the lower end is arranged by inclining downward and outward, the inclined fixing nail has a certain orthotopic thrust trend for the dislocated vertebrae when penetrating into the vertebrae, and has better orthotopic effect by cooperating with the forward or backward adjustment of the supporting lobes; to avoid the fixing nail from loosening, the locking nail is arranged at the fixing hole of the lateral lobe to fasten the fixing hole, and the locking hole is locally connected to the fixing hole, namely, a local arc section of the locking hole and a local arc section of the fixing hole form an overlap region; when the complete convex arc section of the locking nail is transferred to the overlap region, an extrusion and close-fitting effect is given to the fixing nail; and when the concave arc section of the locking nail is transferred to the overlap region, the fixing nail could just penetrate through the concave cavity of the concave arc section, therefore, the locking structure could enable the fixing nail to penetrate into conveniently, and then, could achieve a close-fitting and positioning effect for the fixing nail by rotating the locking nail through the convex ring section thereof.

Further, the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an L-shaped structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole. The supporting lobe is mounted in the mounting cavity of the body frame through fins, and the front end and the rear end of the supporting lobe are respectively in positioning fit with the front and rear cavities of the mounting cavity.

Further, the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an L-shaped structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole; and the supporting lobe further comprises an antiskid bump structure formed on the outside end surface of the body structure, and the antiskid bump structure is continuously distributed in a pyramid shape. The pyramid-shaped bump structure on the supporting lobe can increase a contact area and play a better antiskid effect.

With adoption of the above solution, the lumbar interbody fusion cage in the disclosure can solve both an intervertebral spacing and dislocation arisen from forward and backward lumbar spondylolisthesis; and moreover, the lumbar interbody fusion cage has easy operation and small pain to patients, and is safer and more reliable.

Further description is made below to the disclosure in combination with drawings.

Figure 1:
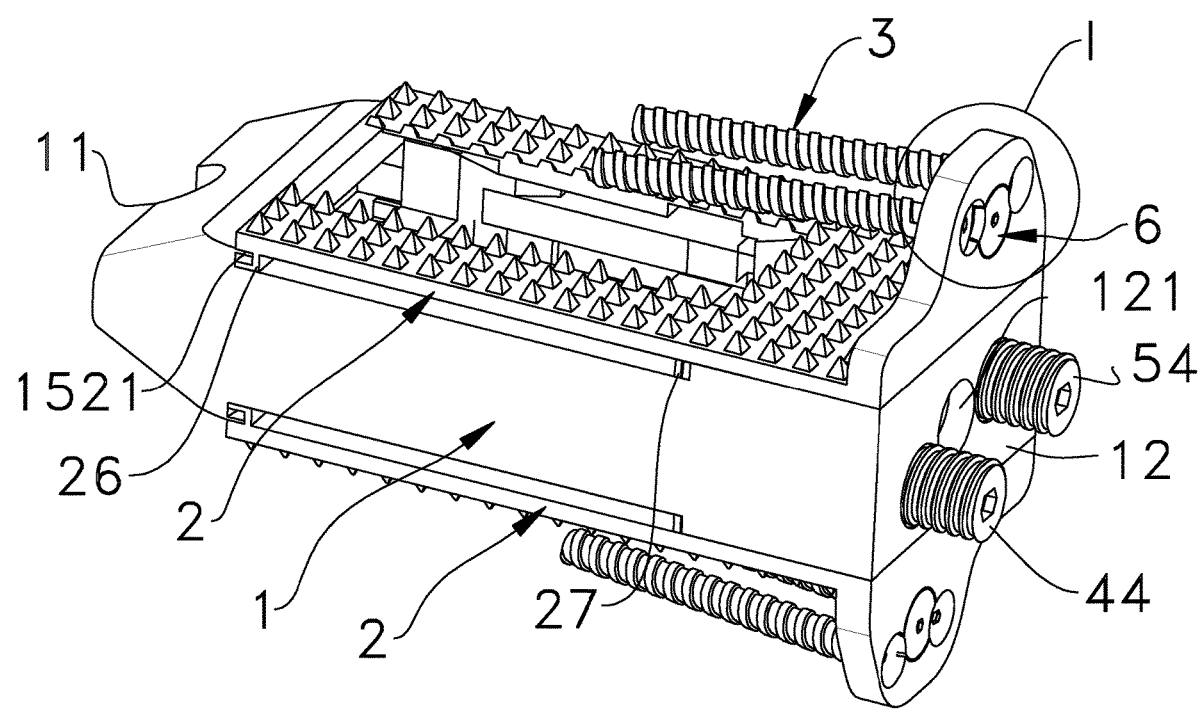
FIG. 1 is a structural diagram of an appearance according to a specific embodiment of the disclosure.

Body frame 1, implantation end 11, tail end 12, bone grafting hole 121, thread hole 122, a front side wall 13, a rear side wall 14, a hollow cavity 15, port 151, mounting cavity 152, reduction moving track 153, external supporting track 154;

supporting lobes 2, center hole 21, lateral lobe 22, fixing hole 221, fitted bevel 23, beveled bump 24, bump fitting surface 241, left limiting bar 26, right limiting bar 27, locking hole 28, antiskid bump structure 29, positioning convex rib 1521, fixing nail 3;

external supporting structure: external supporting frame 4, guide bar 41, abutted bevel 42, operation section 44, thread portion 441, rivet 442;

reduction moving structure: reduction support 5, guide bar 51, forward wedge-shaped surface 52, backward wedge-shaped surface 53, operation section 54, thread portion 541, rivet 542;

locking nail 6, convex arc section 61, internal concave arc section 62.

DETAILED DESCRIPTION OF THE PREFERRED EMBODIMENTS

Figure 2:
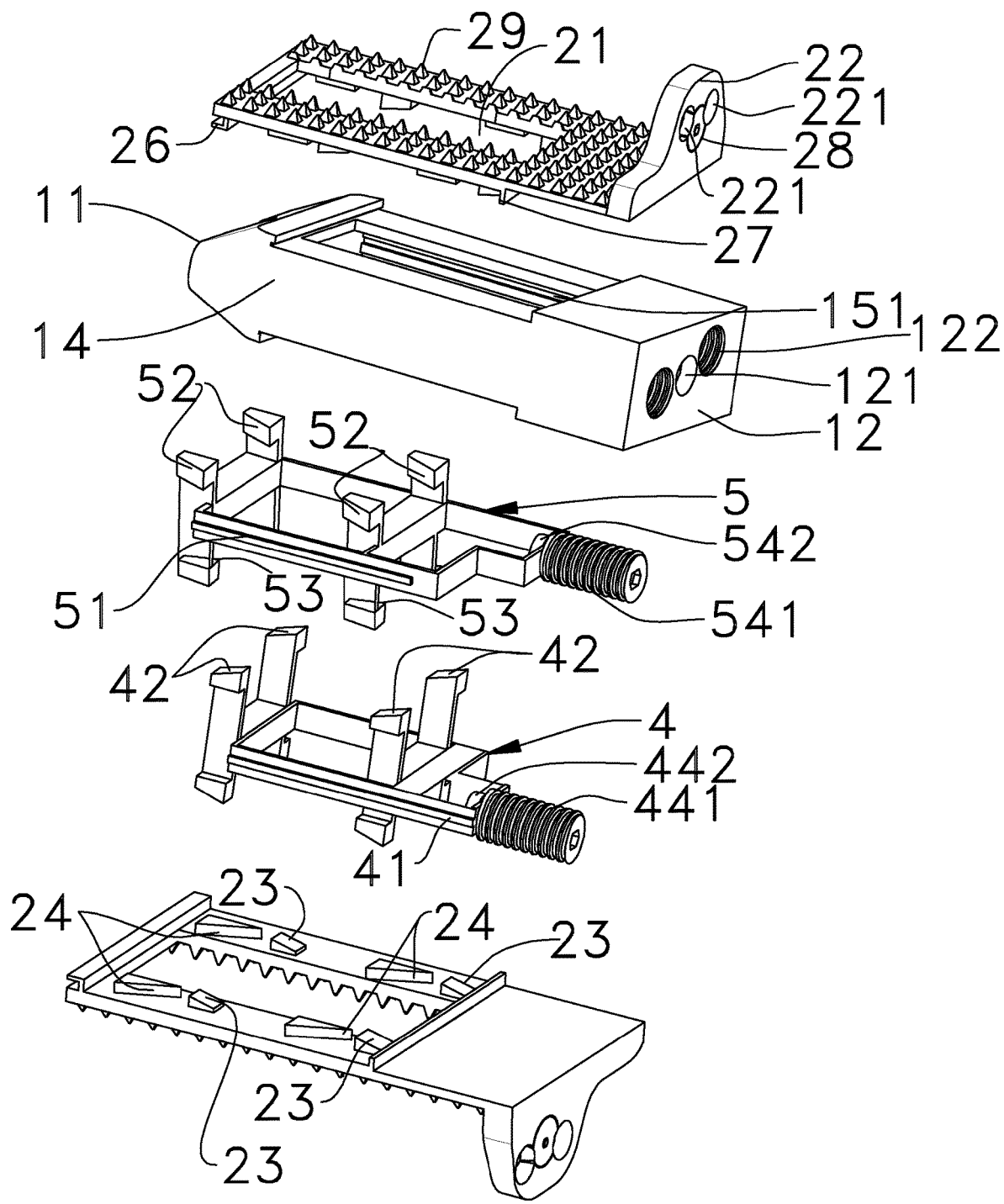
FIG. 2 is an exploded diagram of a structure according to a specific embodiment of the disclosure.
Figure 3:
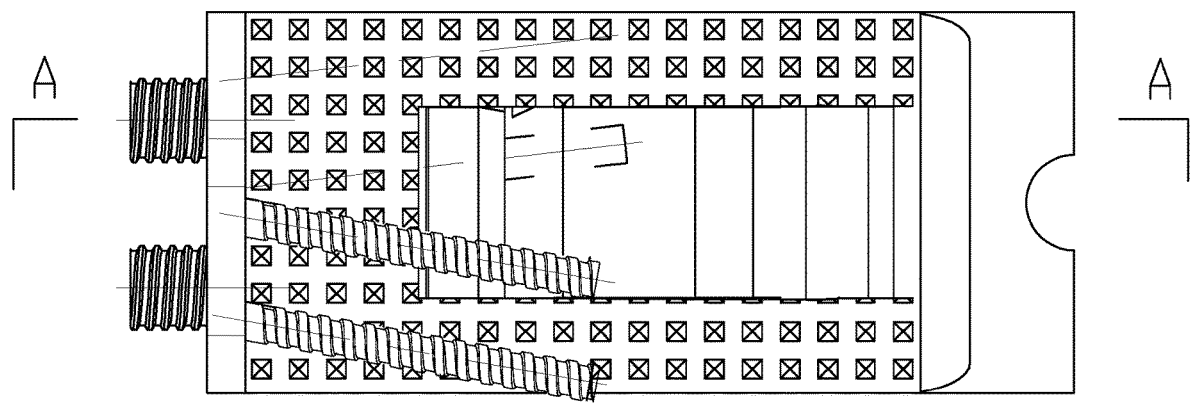
FIG. 3 is a top view according to a specific embodiment of the disclosure.
Figure 4:
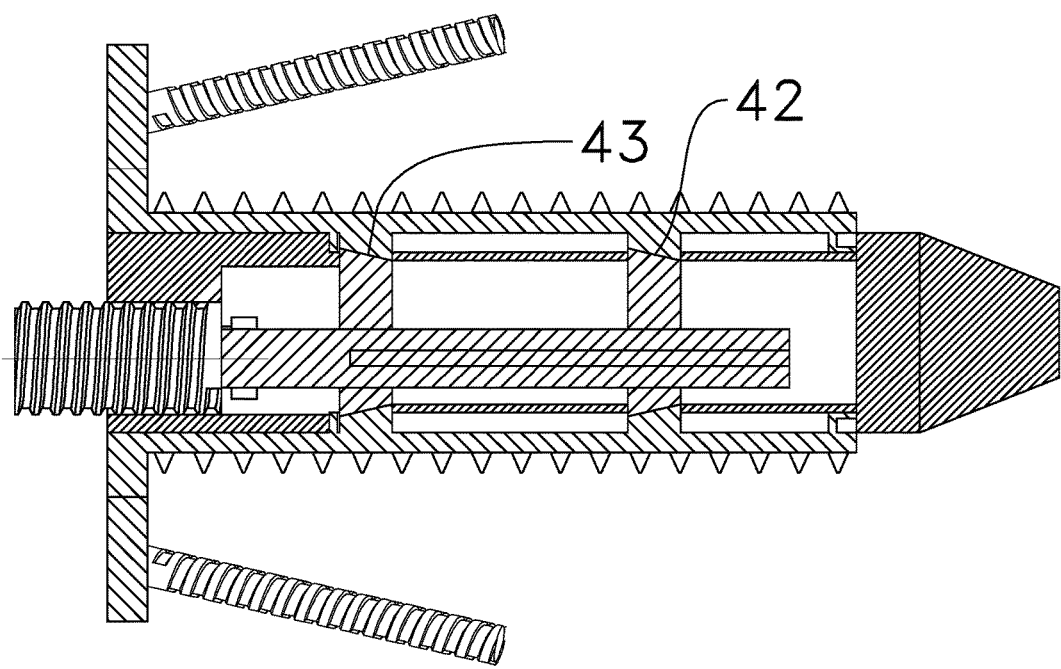
FIG. 4 is an A-A section view in FIG. 3 according to a specific embodiment of the disclosure, which shows a corresponding structure for an internal abutted bevel and a fitted bevel of an external supporting structure.
Figure 5:
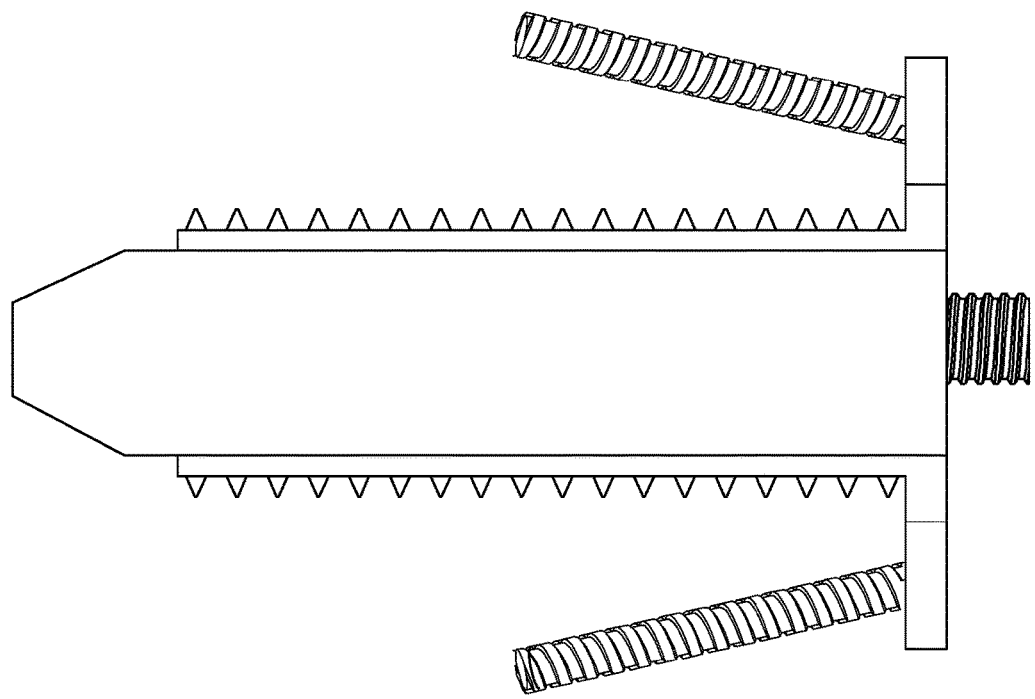
FIG. 5 is a side view according to a specific embodiment of the disclosure.
Figure 6:
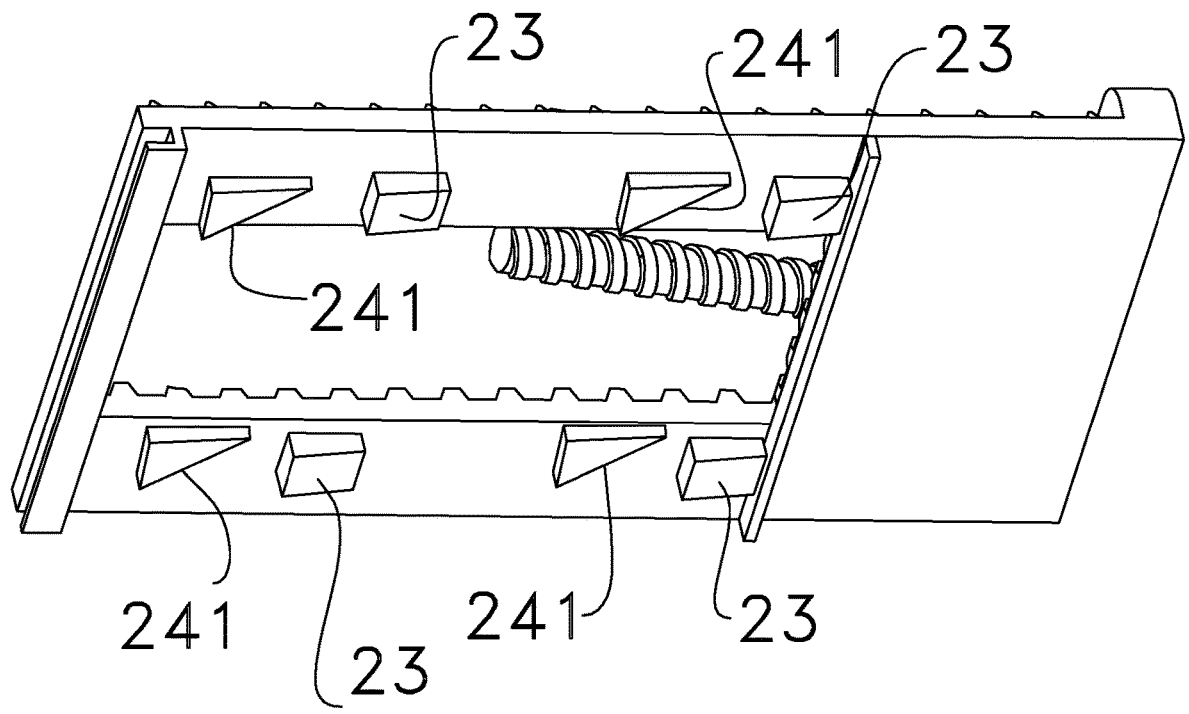
FIG. 6 a schematic diagram for a structure of an internal end surface of a supporting lobe located on the upper end surface of a body frame according to a specific embodiment of the disclosure.
Figure 7:
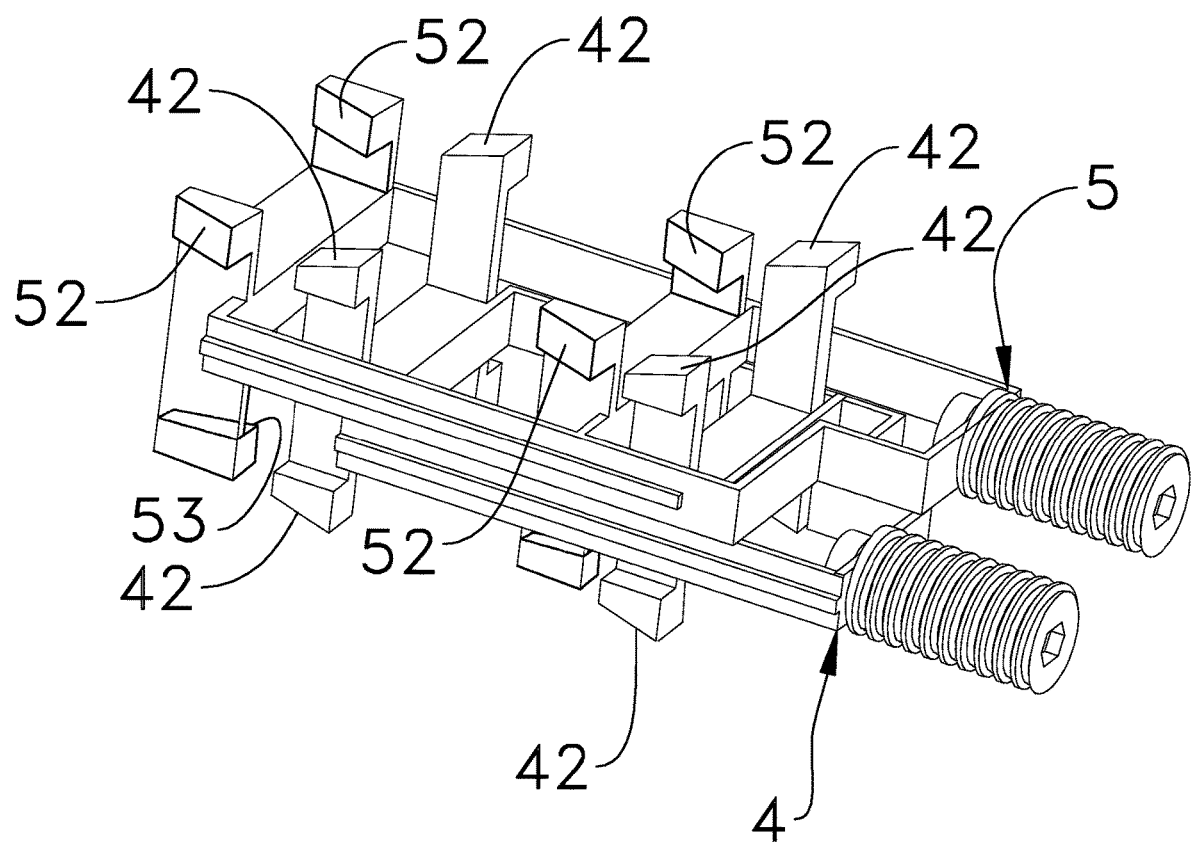
FIG. 7 is a schematic diagram for an up-and-down stacking and mounting structure of a reduction moving structure and an external supporting structure according to a specific embodiment of the disclosure.
Figure 8:
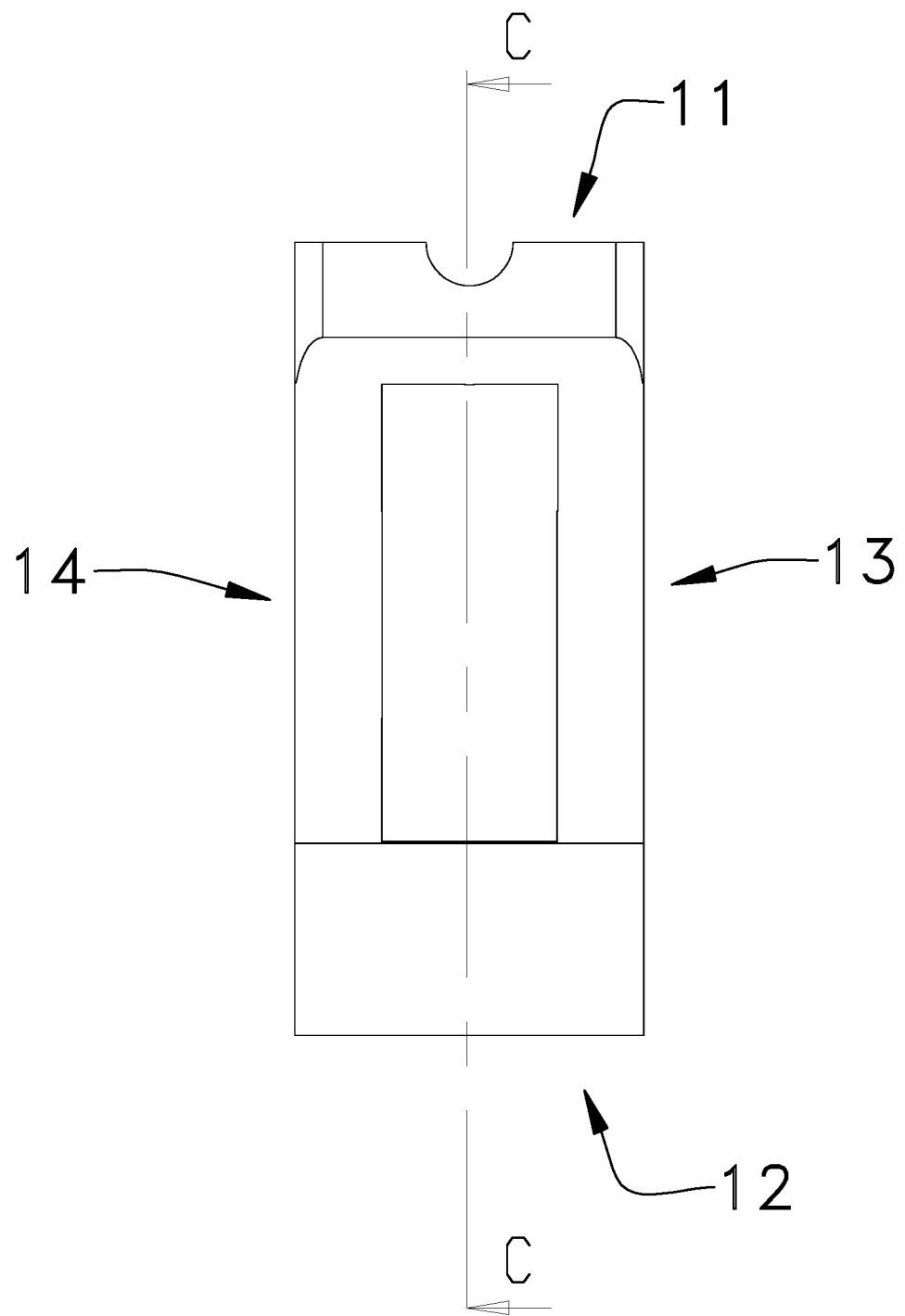
FIG. 8 is a top view of a body frame according to a specific embodiment of the disclosure.
Figure 9:
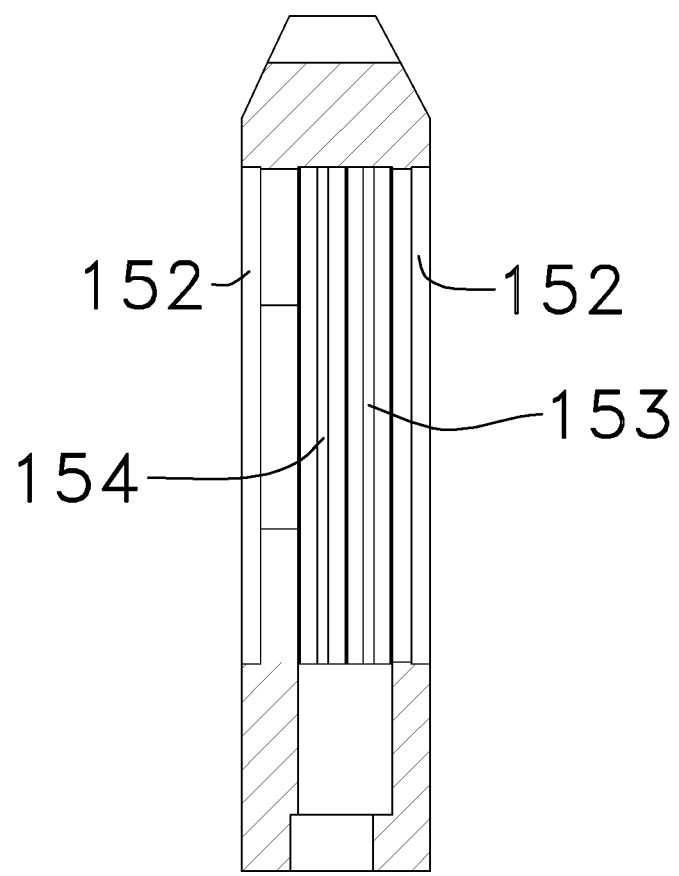
FIG. 9 is a C-C section view in FIG. 8 according to a specific embodiment of the disclosure, which shows distribution structures of a mounting cavity, a reduction moving track and an external supporting track in a body frame.
Figure 10:
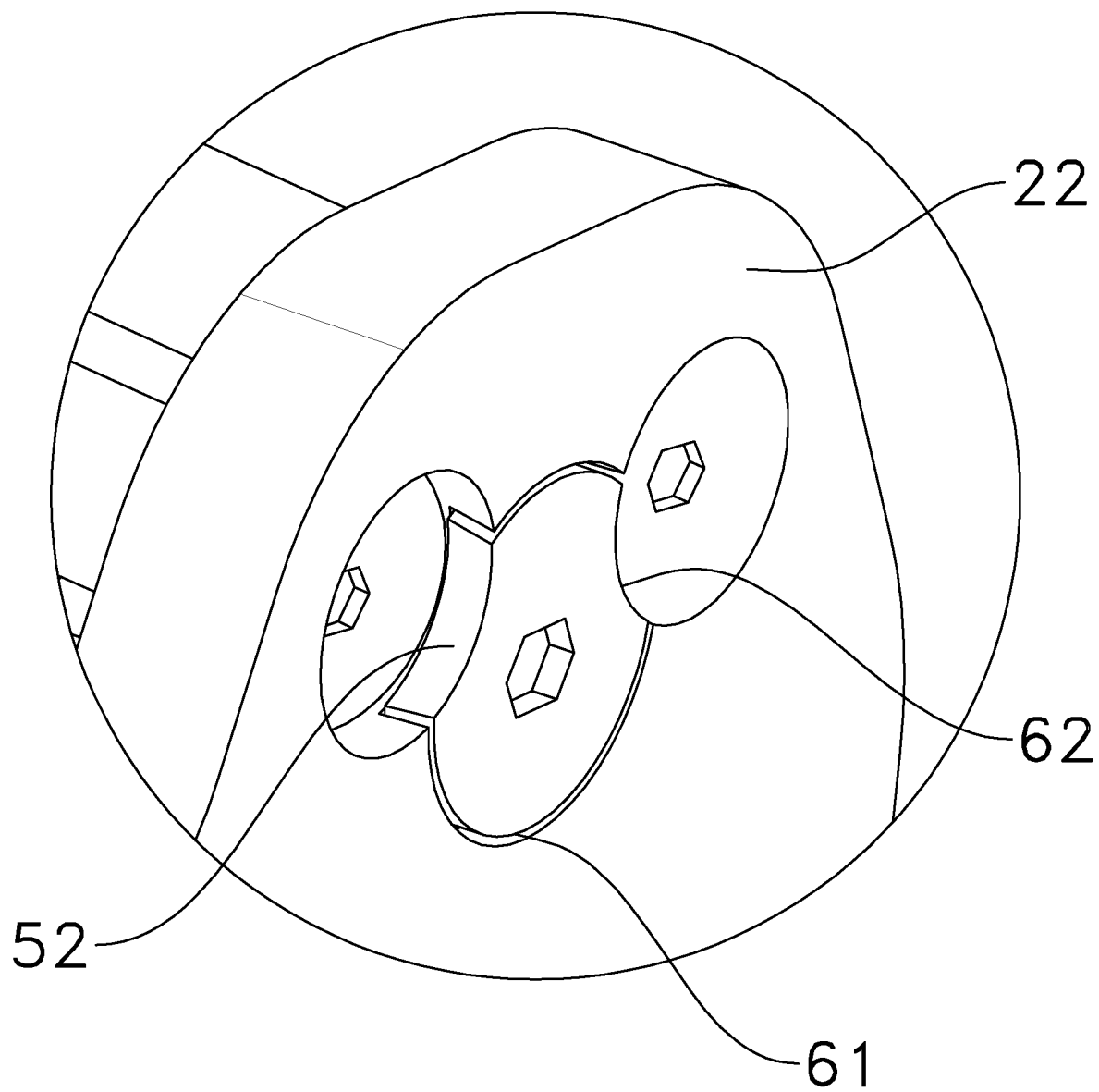
FIG. 10 is an enlarged drawing of local I in FIG. 1 according to a specific embodiment of the disclosure.
Figure 11:
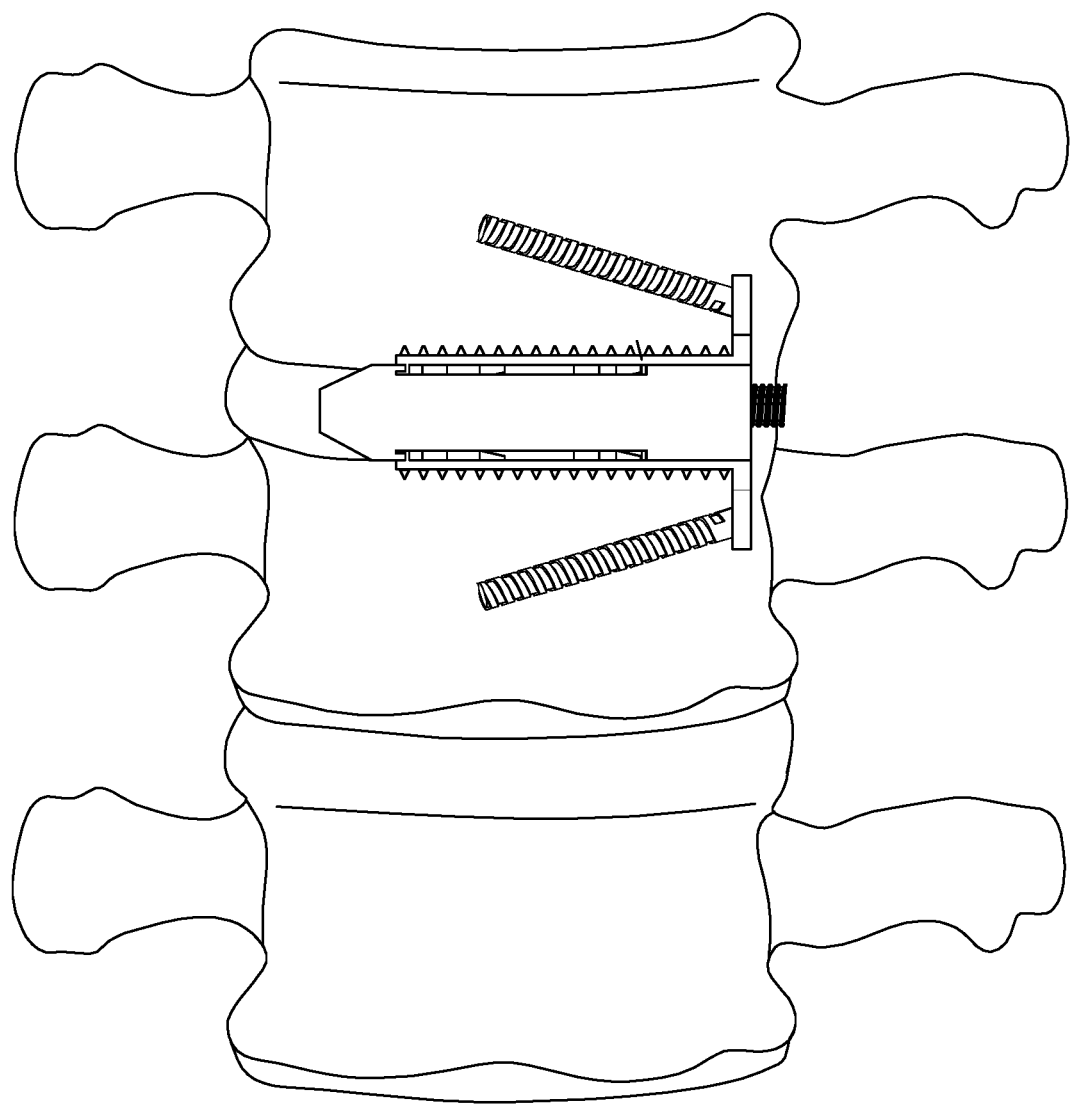
FIG. 11 is a schematic diagram of a structure inserted between upper and lower sections of vertebrae according to a specific embodiment of the disclosure.

A specific embodiment of the disclosure, as shown in FIGS. 1-11, is a lumbar interbody fusion cage for treating lumbar spondylolisthesis via a lateral approach, comprising a body frame 1, supporting lobes 2 and a fixing nail 3, wherein the body frame 1 comprises an implantation end 11 and a tail end 12, a frame body structure having a hollow cavity 15 is formed between the implantation end 11 and the tail end 12 through a connection of a front side wall 13 and a rear side wall 14, a bone grafting hole 121 connected to the hollow cavity 15 is formed at the tail end 12, and the supporting lobes 2 are distributed on the upper and lower end surfaces of the body frame 1 and are provided with a center hole 21 connected to the hollow cavity 15; an external supporting structure for driving the supporting lobes 2 to externally expand towards the upper and lower end surfaces and a reduction moving structure for driving the two supporting lobes 2 to move towards the front side wall 13 and return are in sliding fit with the body frame 1; the hollow cavity 15 comprises two ports 151 located on the upper and lower end surfaces of the body frame 1, and a mounting cavity 152 fitted with the supporting lobe 2, an external supporting track 154 fitted with the external supporting structure and a reduction moving track 153 fitted with the reduction moving structure are distributed between the two ports 151 of the upper and lower end surfaces; and the supporting lobes 2 are in close fit with the left and right inner walls of the mounting cavity 152, (the left side or the left end involved in the text refers to the direction of the implantation end 11, the right side or the right end refers to the direction of the tail end 12, the front side or the front end refers to the direction of the front side wall 13, and the rear side or the rear end refers to the direction of the rear side wall 14) and in clearance fit with the upper and lower inner walls of the mounting cavity 152, a lateral lobe 22 is arranged at a side that the supporting lobe 2 is close to the tail end 12 of the body frame 1 and is equipped with a fixing hole 221, a fixing nail 3 slanted above a rear side is fitted in the fixing hole 221 of the lateral lobe 22 located on the upper end surface, and a fixing nail 3 slanted below a front side is fitted in the fixing hole 221 of the lateral lobe 22 located on the lower end surface.

The external supporting structure comprises an external supporting frame 4; the external supporting frame 4 is equipped with a guide bar 41 which is in sliding fit with the external supporting track 154, two groups of abutted bevels 42 are respectively arranged on the upper and lower end surfaces of the external supporting frame 4 and respectively located at the left side end and the right side end of the external supporting frame 4, the two abutted bevels 42 are arranged at the upper part and the lower part of the left side end and also arranged at the upper part and the lower part of the right side end respectively, the abutted bevels 42 on the upper and lower end surfaces are respectively formed by extending the left side end to incline upward or downward along the right side end, a corresponding fitted bevel 23 is arranged on the internal end surface of the supporting lobe 2, an operating section 44 is arranged on the external supporting frame 4 and is in thread spinning fit with a thread hole 122 at the tail end 12 of the body frame 1, and the abutted bevel 42 of the external supporting frame 4 is abutted against the fitted bevel 23 with a positive movement of a thread of the operation section 44 to drive the supporting lobe 2 to externally support and move to form an external expansion structure of the supporting lobe; the abutted bevel 42 moves forward when the external supporting frame 4 rotates clockwise with the operation section 44, the external supporting frame 44 extrudes the fitted bevel 23 on the internal end surface of the supporting lobe 2 through the abutted bevel 42 thereof to enable the two supporting lobes 2 to continue to externally expand upward and downward respectively, and when the external supporting frame 4 rotates anticlockwise with the operation section 44, the supporting lobe 2 of the abutted bevel 42 of the external supporting frame 4 moves back to an original position towards an inside by suffering from an extrusion effect of the upper and lower sections of vertebrae, thereby achieving the return of the supporting lobe 2.

The reduction moving structure comprises a reduction support 5, the reduction support 5 is equipped with a guide bar 51 which is fitted with the reduction moving track 153, two groups of wedge-shaped blocks are arranged on the reduction support 5, and a forward wedge-shaped surface 52 and a backward wedge-shaped surface 53 are respectively arranged on the two groups of wedge-shaped blocks, respectively face towards the rear side wall 14 and the front side wall 13, and extend by inclining from the left side end to the right side end; four wedge-shaped blocks in the embodiment are respectively located on the front side wall and the rear side wall of the reduction support 5; beveled bumps 24 fitted with the respective forward wedge-shaped surface 52 and the backward wedge-shaped surface 53 thereof are arranged on the internal end surface of the supporting lobe 2, a bevel of the beveled bump 24 forms a bump fitting surface 241, and the bump fitting surface 241 is abutted against the wedge-shaped surface 52; and an operation section 54 which is in thread spinning with another thread hole 122 of the tail end 12 of the body frame 1 is arranged on the reduction support 5, and the upper and lower supporting lobes 2 are abutted against the beveled bumps 24 through the forward wedge-shaped surface 52 and the backward wedge-shaped surface 53 with a positive thread movement of the operation section 54 to drive the two supporting lobes 2 to respectively move towards the front side wall 13 and the rear side wall 13 to form a reduction structure of the supporting lobe.

The reduction support 5 and the external supporting frame 4 are in a hollow frame body structure, and are stacked up and down; the reduction moving track 153 and the external supporting track 154 are distributed up and down and are respectively adapted to the guide bar 51 of the reduction support 5 and the guide bar 41 of the external supporting frame 4; abutted blocks are arranged at the left end and the right end of the external supporting frame 4; the abutted bevels 42 are arranged on the abutted blocks; the wedge-shaped surface of the reduction support 5 is arranged on the wedge-shaped blocks; and the abutted blocks are located inside a space formed by the wedge-shaped blocks at the left and right ends, and a gap is formed between the abutted blocks and the wedge-shaped blocks, comprises a front end gap, a rear end gap, a left side gap and a right side gap, and provides a mobile space for upper and lower external expansion and forward and backward reduction movement of the supporting lobe 2.

A mounting hole is formed at the rear side of the external supporting frame 4; the operation section 44 of the external supporting frame 4 comprises a thread portion 441 and a connecting shaft portion, one end of the connecting shaft portion of the external supporting frame 4 penetrates through the mounting hole of the external supporting frame 4 and then is fixed with a rivet 442, and the other end thereof is integrally connected with the thread portion 441; a mounting hole is formed at the rear side of the reduction support 5; the operation section 54 of the reduction section 5 comprises a thread portion 541 and a connecting shaft portion, one end of the connecting shaft portion of the operation section 54 penetrates through the mounting hole of the reduction support 5 and is fixed with a rivet 542, and the other end thereof is integrally connected with the thread portion 541; and two thread holes 122 which are respectively in thread fit with the operation section 44 of the external supporting frame 4 and the operation section 54 of the reduction support 5 are formed at the tail end 12 of the body frame 1.

The lateral lobe 22 is equipped with a locking structure of the fixing nail 3, the locking structure comprises a locking nail 6, the lateral lobe 22 is equipped with a locking hole 28 for accommodating the locking nail 6, the side wall of the locking hole 28 is locally connected to the fixing hole 221, and one end of the locking nail 6 penetrates through the locking hole 28 and is connected to the lateral lobe 22 by rotating with a rivet, the side of the locking nail 6 comprises a convex arc section 61 and a concave arc section 62 formed through cutting, the concave arc section 62 is adapted to a lateral arc-shaped surface of a head of the fixing nail 3 located in a neighboring fixing hole 221 and is in clearance fit with the same, and the convex arc section 61 of the locking nail 6 is in close extrusion fit with the lateral arc-shaped surface of the head of the fixing nail 3.

The supporting lobe 2 comprises a body structure, the right side end of the body structure is bent to extend upward or downward to form the lateral lobe 22, a left limiting bar 26 and a right limiting bar 27 which are in limiting fit with a left cavity and a right cavity of the mounting cavity 152 are respectively arranged on the left and right of the internal end surface of the body structure, the left limiting bar 26 presents an L-shaped structure, a U-shaped limiting slot is formed between the left limiting bar 26 and the left side of the internal end surface of the body structure, a positioning convex rib 1521 fitted with the limiting slot is arranged on the inner wall of the left cavity of the mounting cavity 152, a gap is formed between the positioning convex rib 1521 and the inner wall of the upper end or the lower end of the limiting slot, and the positioning convex rib 1521 is in axial positioning fit with the limiting slot along the bone grafting hole 121. The supporting lobe 2 further comprises an antiskid bump structure 29 formed on the outside end surface of the body structure, and the antiskid bump structure 29 is continuously distributed in a pyramid shape.

The disclosure is not limited to the above specific embodiments. Persons of ordinary skill in the art can implement the disclosure with many other specific embodiments according to the content claimed by the disclosure, or all simple changes or modifications made with the design structure and thought of the disclosure are included in the protection scope of the disclosure.

The invention claimed is:

1. A lumbar interbody fusion cage for treating lumbar spondylolisthesis via a lateral approach, comprising:
    a body frame, supporting lobes and a fixing nail, wherein the body frame comprises an implantation end and a tail end, a frame body structure having a hollow cavity is formed between the implantation end and the tail end through a connection of a front side wall and a rear side wall, a bone grafting hole connected to the hollow cavity is formed at the tail end, the supporting lobes are distributed on the upper and lower end surfaces of the body frame, and each of the supporting lobes is provided with a center hole connected to the hollow cavity; an external supporting structure for driving the supporting lobes to externally expand towards the upper and lower end surfaces and a reduction moving structure for driving the two supporting lobes to move towards the front side wall and the rear side wall respectively are in sliding fit with the body frame; the hollow cavity comprises two ports located on the upper and lower end surfaces of the body frame, and a mounting cavity fitted with the supporting lobe, an external supporting track fitted with the external supporting structure and a reduction moving track fitted with the reduction moving structure are distributed between the two ports of the upper and lower end surfaces; the supporting lobes are in close fit with the left and right inner walls of the mounting cavity and in clearance fit with the upper and lower inner walls of the mounting cavity, a lateral lobe is arranged at a side that the supporting lobe is close to the tail end of the body frame and is equipped with a fixing hole, a fixing nail slanted above a rear side is fitted in the fixing hole of the lateral lobe located on the upper end surface, and a fixing nail slanted below a front side is fitted in the fixing hole of the lateral lobe located on the lower end surface.

2. The lumbar interbody fusion cage for treating lumbar spondylolisthesis via the lateral approach according to claim 1, wherein the external supporting structure comprises an external supporting frame; the external supporting frame is equipped with a guide bar which is in sliding fit with the external supporting track, two groups of abutted bevels are respectively arranged on the upper and lower end surfaces of the external supporting frame and respectively located at the left side end and the right side end of the external supporting frame, the two groups of abutted bevels on the upper and lower end surfaces extend towards the left side end in a slanting way, a corresponding fitted bevel is arranged on the internal end surface of the supporting lobe, an operation section is arranged on the external supporting frame and is in thread spinning fit with the tail end of the body frame, and the abutted bevel of the external supporting frame is abutted against the fitted bevel with a positive movement of a thread of the operation section to drive the supporting lobe to externally support and move to form an external expansion structure of the supporting lobe; the reduction moving structure comprises a reduction support, the reduction support is equipped with a guide bar which is fitted with the reduction moving track, two groups of wedge-shaped blocks are arranged on the reduction support, two groups of wedge-shaped surfaces are formed on the two groups of wedge-shaped blocks and respectively extend towards the rear side wall and the front side wall from the left side end to the right side end in a slanting way, beveled humps fitted with the wedge-shaped surfaces are arranged on the internal end surface of the supporting lobe, a bevel of the beveled bump forms a hump fitting surface, and the hump fitting surface is abutted against the wedge-shaped surface; and an operation section which is in thread spinning with the tail end of the body frame is arranged on the reduction support, and the two supporting lobes on the upper and lower end surfaces are abutted against the beveled bumps through the wedge-shaped surface with a positive thread movement of the operation section to drive the two supporting lobes to respectively move towards the front side wall and the rear side wall to form a reduction structure of the supporting lobe.

3. The lumbar interbody fusion cage for treating lumbar spondylolisthesis via the lateral approach according to claim 2, wherein the reduction support and the external supporting frame are in a hollow frame body structure, and are stacked up and down; the reduction moving track and the external supporting track are distributed up and down and are respectively adapted to the guide bar of the reduction support and the guide bar of the external supporting frame; abutted blocks are arranged at the left end and the right end of the external supporting frame; the abutted bevels are arranged on the upper end surface or the lower end surface of the abutted blocks; the wedged-shaped blocks are arranged at the left end and the right end of the reduction support; the wedge-shaped surface is arranged at the left side or the right side of the wedge-shaped block; and the abutted blocks are located in a space formed by the wedge-shaped blocks at the left and right ends, and a gap is formed between the abutted blocks and the wedge-shaped blocks and comprises a front end gap, a rear end gap, a left side gap and a right side gap.

4. The lumbar interbody fusion cage for treating lumbar spondylolisthesis via the lateral approach according to claim 2, wherein a mounting hole is formed at the rear side of the external supporting frame; the operation section of the external supporting frame comprises a thread portion and a connecting shaft portion, one end of the connecting shaft portion of the external supporting frame penetrates through the mounting hole of the external supporting frame and then is fixed with a rivet, and the other end thereof is integrally connected with the thread portion; a mounting hole is formed at the rear side of the reduction support; the operation section of the reduction Section comprises a thread portion and a connecting shaft portion, one end of the connecting shaft portion of the reduction support penetrates through the mounting hole of the external supporting flame and then is fixed with a rivet, and the other end thereof is integrally connected with the thread portion of the reduction support; and two thread holes which are respectively in thread fit with the operation section of the external supporting frame and the operation section of the reduction support are formed at the tail end of the body frame.

5. The lumbar interbody fusion cage for treating lumbar spondylolisthesis via the lateral approach according to claim 1, wherein the lateral lobe is equipped with a locking structure of the fixing nail, the locking structure comprises a locking nail, the lateral lobe is equipped with a locking hole for accommodating the locking nail, the side wall of the locking hole is locally connected to the fixing hole, and one end of the locking nail penetrates through the locking hole and is connected to the lateral lobe by rotating with a rivet, the side of the locking nail comprises a convex arc section and a concave arc section formed through cutting, the concave arc section is adapted to a lateral arc-shaped surface of a head of the fixing nail located in a neighboring fixing hole and is in clearance fit with the same, and the convex arc section of the locking nail is in close extrusion fit with the lateral arc-shaped surface of the head of the fixing nail.

6. The lumbar interbody fusion cage for treating lumbar spondylolisthesis via the lateral approach according to claim 4, wherein the lateral lobe is equipped with a locking structure of the fixing nail, the locking structure comprises a locking nail, the lateral lobe is equipped with a locking hole for accommodating the locking nail, the side wall of the locking hole is locally connected to the fixing hole, and one end of the locking nail penetrates through the locking hole and is connected to the lateral lobe by rotating with a rivet, the side of the locking nail comprises a convex arc section and a concave arc section formed through cutting, the concave arc section is adapted to a lateral arc-shaped surface of a head of the fixing nail located in a neighboring fixing hole and is in clearance fit with the same, and the convex arc section of the locking nail is in close extrusion fit with the lateral arc-shaped surface of the head of the fixing nail.

7. The lumbar interbody fusion cage for treating lumbar spondylolisthesis via the lateral approach according to claim 1, wherein the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an L-shaped structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole.

8. The lumbar interbody fusion cage for treating lumbar spondylolisthesis via the lateral approach according to claim 4, wherein the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an L-shaped structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole.

9. The lumbar interbody fusion cage for treating lumbar spondylolisthesis via the lateral approach according to claim 5, wherein the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an L-shaped structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole.

10. The lumbar interbody fusion cage for treating lumbar spondylolisthesis via the lateral approach according to claim 6, wherein the supporting lobe comprises a body structure, the right side end of the body structure is bent to extend upward or downward to form the lateral lobe, a left limiting bar and a right limiting bar which are in limiting fit with a left cavity and a right cavity of the mounting cavity are respectively arranged on the left and right of the internal end surface of the body structure, the left limiting bar presents an shaped structure, structure, a U-shaped limiting slot is formed between the left limiting bar and the left side of the internal end surface of the body structure, a positioning convex rib fitted with the limiting slot is arranged on the inner wall of the left cavity of the mounting cavity, a gap is formed between the positioning convex rib and the inner wall of the upper end or the lower end of the limiting slot, and the positioning convex rib is in axial positioning fit with the limiting slot along the bone grafting hole; and the supporting lobe further comprises an antiskid bump structure formed on the outside end surface of the body structure, and the antiskid bump structure is continuously distributed in a pyramid shape.

* * * * *